United States Patent [19]

Bartles-Keith et al.

[11] 4,067,871
[45] Jan. 10, 1978

[54] 1-NITROSO-1,2,3,4-TETRAHYDROQUINO-LINE AND 1-NITROSO-INDOLINE COMPOUNDS

[75] Inventors: James R. Bartles-Keith, Lexington; Mary T. Burgess, Boston; Jean B. Rogers, Carlisle, all of Mass.

[73] Assignee: Polaroid Corporation, Cambridge, Mass.

[21] Appl. No.: 721,858

[22] Filed: Sept. 9, 1976

Related U.S. Application Data

[63] Continuation-in-part of Ser. No. 592,397, July 2, 1975, abandoned.

[51] Int. Cl.² .................. C07D 215/58; C07D 209/12
[52] U.S. Cl. ........................ 260/287 T; 260/239 BB; 260/283 CN; 260/287 CF; 260/288 CF; 260/326.11 R; 548/359; 96/66 HD
[58] Field of Search .... 260/287 T, 283 CN, 326.11 R

[56] References Cited

PUBLICATIONS

Jones et al., Tetrahedron, vol. 21, pp. 2951–2971 (1965).

Primary Examiner—Paul M. Coughlan, Jr.
Assistant Examiner—Mary Vaughn
Attorney, Agent, or Firm—Sybil A. Campbell

[57] ABSTRACT

This invention relates to N-nitroso compounds having the formula

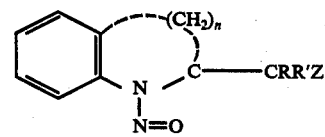

wherein R and R' each are selected from hydrogen and alkyl, Z is —CN or —COOR" wherein R" is alkyl and $n$ is a positive integer from 1 to 7. These compounds are useful as intermediates in the preparation of photographic silver halide developing agents.

11 Claims, No Drawings

1-NITROSO-1,2,3,4-TETRAHYDROQUINOLINE AND 1-NITROSO-INDOLINE COMPOUNDS

CROSS-REFERENCE TO RELATED PATENT APPLICATIONS

This application is a continuation-in-part of copending U.S. patent application Ser. No. 592,397 filed July 2, 1975, now abandoned.

BACKGROUND OF THE INVENTION

1. Field of the Invention

This invention relates to novel N-heterocyclic compounds possessing a nitroso group on the heterocyclic N atom, which compounds are useful as intermediates in the preparation of photographic silver halide developing agents.

2. Description of the Prior Art

In recent years, there has been a growing interest in heterocyclic photographic developing agents, i.e., developers containing a heterocyclic ring as part of their structure. Some of these developing agents have the conventional hydroxyl or amino developing groups substituted on adjacent carbon atoms of a heterocyclic ring to provide structures similar to those of the developing agents in the aliphatic and aromatic series. Still other heterocyclic developing agents have one of the functional developing groups included as part of the heterocyclic ring. Copending U.S. patent application Ser. No. 721,859 of Stanley M. Bloom, which is a continuation-in-part of application Ser. No. 592,398 filed July 2, 1975, now abandoned, which, in turn, is a continuation-in-part of application Ser. No. 451,740 filed Mar. 18, 1974, now abandoned, discloses and claims the use of certain tricyclic developing agents of the latter type, i.e., developing agents having one of the functional developing groups included as part of a heterocyclic ring.

N-nitrosos compounds useful as intermediates in the synthesis of the aforementioned tricyclic developing agents comprise the subject matter of the present invention.

SUMMARY OF THE INVENTION

It is the primary object of the present invention to provide certain N-heterocyclic compounds possessing a nitroso group on the heterocyclic N atom.

It is another object of the present invention to provide heterocyclic compounds useful as intermediates in the preparation of photographic developing agents.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

Specifically, the compounds provided by the present invention may be represented by the formula

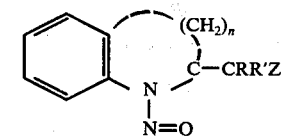
(I)

wherein R and R' each are hydrogen or lower alkyl having 1 to 4 carbon atoms, Z is —CN or —COOR" wherein R" is alkyl, usually lower alkyl having 1 to 4 carbon atoms and $n$ is a positive integer from 1 to 7.

In a preferred embodiment, $n$ is 1 or 2 and the subject compounds are N-nitroso derivatives of indolines or 1,2,3,4-tetrahydroquinolines. The preferred compounds may be represented by the formula

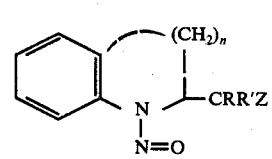
(II)

wherein R, R' and Z have the same meaning given in formula I above and $n$ is 1 or 2.

Specific examples of preferred N-nitroso compounds within the scope of the present invention are as follows:

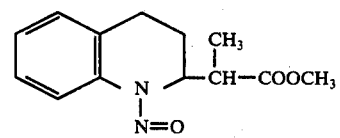
(1)

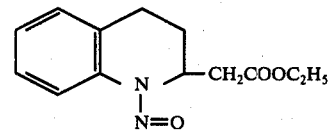
(2)

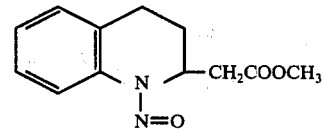
(3)

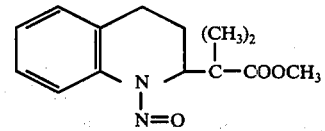
(4)

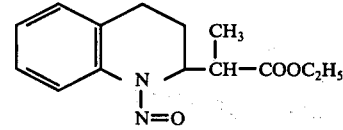
(5)

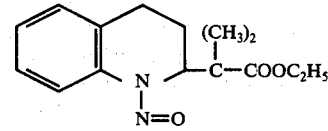
(6)

(7)

[Structure: 1,2,3,4-tetrahydroquinoline with N-N=O, 2-position substituent CH(C₂H₅)-COOC₂H₅]

(8)

[Structure: 1,2,3,4-tetrahydroquinoline with N-N=O, 2-position substituent CH₂COOC₃H₇]

(9)

[Structure: 1,2,3,4-tetrahydroquinoline with N-N=O, 2-position substituent CH₂CN]

(10)

[Structure: 1,2,3,4-tetrahydroquinoline with N-N=O, 2-position substituent C(CH₃)₂-CN]

(11)

[Structure: indoline with N-N=O, 2-position substituent CH₂-COOC₂H₅]

(12)

[Structure: indoline with N-N=O, 2-position substituent CH(CH₃)-COOCH₃]

(13)

[Structure: indoline with N-N=O, 2-position substituent CH(CH₃)₂-COOC₂H₅]

(14)

[Structure: indoline with N-N=O, 2-position substituent CH₂CN]

(15)

[Structure: indoline with N-N=O, 2-position substituent C(CH₃)₂-CN]

The subject compounds may be synthesized by nitrosation of a compound having the formula (III)

[Structure: benzo-fused ring with NH and C-CRR'Z with (CH₂)ₙ bridge]

wherein R, R', n and Z have the same meaning given in formula I above. Usually, the nitrosation is carried out by adding an aqueous solution of sodium nitrite to a solution of the selected starting compound in dilute aqueous hydrochloric acid at room temperature and then isolating the corresponding N-nitroso compound from the reaction solution. Despite the bulky substituent in the 2-position of the starting compound, it has been found that nitrosation is efficient giving the N-nitroso compound as the major product in all cases.

The acid ester and the nitrile starting materials may be prepared in a conventional manner. For example, acid esters, such as, ethyl 1,2,3,4-tetrahydro-2-quinolylacetate and nitriles, such as, 1,2,3,4-tetrahydro-2-quinolylacetonitrile are known and may be synthesized according to the procedures reported by G. Jones and J. Wood, Tetrahedron, Vol. 21, pp. 2951-2971 (1965). The indoline esters and nitriles may be prepared, for example, by reduction of the corresponding indoles.

The following examples illustrate the preparation of compounds within the scope of the invention and are given for purposes of illustration only.

EXAMPLE 1

Preparation of

[Structure: 1,2,3,4-tetrahydroquinoline with N-N=O, 2-position substituent CH₂COOC₂H₅]:

A colorless solution of 16 gms. of ethyl 1,2,3,4-tetrahydro-2-quinolylacetate in 150 mls. of 10% hydrochloric acid was stirred at room temperature, and 5 gms. of sodium nitrite in 30 mls. of water were added dropwise over a period of about 20 minutes. No heat was evolved. After addition was complete, stirring was continued for another 20 minutes. The solution turned orange, and a dark orange oil precipitated. The orange oil was taken up in benzene, and the benzene solution was washed to neutral, dried and stripped. The dark orange oil was then taken up in hexane, and after boiling, the solution was decanted from the brown insoluble residue. The hexane solution was then cooled in an ice bath and decanted from the yellow-brown oil that formed. The decanted solution was stripped to give the title compound as a yellow oil, 14 gms., $\nu_{max}$ 1440 cm$^{-1}$.

EXAMPLE 2

Preparation of

[Structure: 1,2,3,4-tetrahydroquinoline with N-N=O, 2-position substituent C(CH₃)₂-COOC₂H₅]:

The procedure of Example 1 was repeated using as the acid ester starting material, the compound

[Structure: 1,2,3,4-tetrahydroquinoline with NH, 2-position substituent C(CH₃)₂-COOC₂H₅]

(1.3 gms) in 15 mls. of 15% hydrochloric acid and 1 gm. of sodium nitrite in 5 mls. of water to give the corresponding N-nitroso intermediate as a yellow oil, $\nu_{max}$ 1460 cm$^{-1}$.

EXAMPLE 3

Preparation of

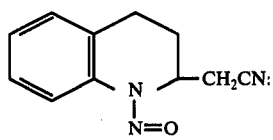

A solution of 9.7 gms. of 1,2,3,4-tetrahydro-2-quinolylacetonitrile in 200 mls. of 10% hydrochloric acid was stirred at room temperature, and 5 gms. of sodium nitrite in 25 mls. of water were added slowly. The resulting solution became a reddish color and then a red-brown oil precipitated. The solution was allowed to stand for about 4 days. The red-brown oil was extracted into benzene, and the benzene solution washed and dried and then stripped to leave about 8 gms. of brown oil. The aqueous reaction solution was made basic and again extracted with benzene to give an additional gram of brown oil. The oils were combined and chromatographed on Florisil using benzene as the eluent. The title compound was collected as an oil, 3 gms., $v_{max}$ 1440 cm$^{-1}$.

EXAMPLE 4

Preparation of

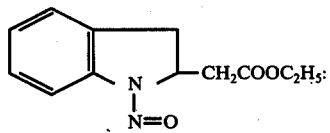

To a 3.3 gm sample (0.016M) of ethyl-2-indolinylacetate was added 40 cc. of 10% hydrochloric acid and the mixture cooled to 10°-20° C. A solution of 3.5 gms of sodium nitrite (0.05M) in 20 cc. of water was added dropwise. Then the mixture was allowed to stir at 10°-20° C. for 1 hour.

The product was extracted into benzene and the benzene layer washed with a little sodium bicarbonate solution. After drying, over sodium sulfate, the benzene solution was filtered and the solvent evaporated on a rotary evaporator. The title compound was obtained as a brown oily solid.

The ethyl-2-indolinylacetate used in the above example was prepared as follows:

a. 22.2 gm (0.17M) of ethylacetoacetate was added dropwise to a well-stirred suspension of 7.6 gm (0.18M) of sodium hydride, (57% in mineral oil) in 300 ml of dry benzene, keeping the mixture in a nitrogen atmosphere. The reaction mixture was stirred for 1 hour under nitrogen. 33.9 gm of o-nitrophenylacetylchloride in 100 cc. dry benzene was added dropwise over a period of approximately 45 minutes. The mixture was allowed to stir for 1 hour at room temperature. The mixture was then diluted with 150 cc. dry benzene and washed twice with 150 cc. water. The benzene layer was dried over anhydrous sodium sulfate. (Additional product can be obtained by acidfying the water layer and extracting with ethyl ether). The solvent was removed and the ethyl-o-nitrophenylacetylacetoacetate product was crystallized by treatment with methanol and recovered as a pale colored material.

b. 30 gm (0.103M) ethyl-o-nitrophenylacetylacetoacetate was added over a period of 15-20 minutes to a saturated ammoniacal ethanol solution (prepared by bubbling NH$_3$ gas into 400 cc. absolute for 15-20 minutes while cooling the solution to 0°-5° C.). The orangy mixture was stirred for 1 hour at 5°-10° C. and then left in the refrigerator overnight. The ethyl-γ-2-nitrophenylacetoacetate crystals formed were filtered and dried in vacuum. Additional solid was obtained after evaporation of the filtrate and washing with water to remove any amide formed.

c. A sample of 12.0 gm (0.048M) of ethyl-γ-2-nitrophenylacetoacetate was dissolved in 200 cc. glacial acetic acid. Approximately 2½ spatulas of 5% Pd/C was added to the solution and the compound was reduced on the Parr hydrogenator. Ethyl-2-indolylacetate was obtained as a dark orangy oily liquid after removal of catalyst and solvent.

d. 8.8 gm (0.04M) of the indole prepared in step (c) was dissolved in 150 cc. glacial acetic acid and cooled to ±20° C. in an ice bath. 2.4 gm of sodium cyanoborohydride was added slowly over a period of 10-15 minutes. The mixture was allowed to stir at 20° C. for 1 hour and then poured into 150 cc. ice water. The product was extracted with ethyl ether and dried over anhydrous sodium sulfate. The ethyl ether was removed leaving ethyl-2-indolinylacetate as a dark oily material which was purified by extraction in petroleum ether/methanol and salt solution.

As noted previously, the N-nitroso compounds of the subject invention are useful as intermediates in the synthesis of photographic developing agents. It has been found that these compounds undergo ring-closure to yield developing agents of the formula:

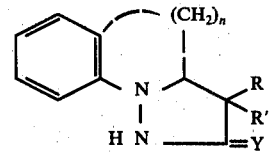

wherein Y is =O or =NH and R, R' and n have the same meaning given formula I above.

Depending upon the particular nitroso compound, ring-closing to the developing agent product may be achieved by reduction alone or by reduction followed by cyclization. For example, ring-closing of the N-nitroso quinoline compounds may be carried out by treating the N-nitroso compounds with zinc dust in a solvent, such as dilute glacial acetic acid, while maintaining the temperature between about 10° and 20° C. The reaction mixture is then stirred at room temperature, the zinc dust removed by filtration and the developing agent product isolated from the filtrate. Ring-closing of the N-nitroso indoline compounds may be carried out by electrolytic reduction followed by heating in quinoline. As an illustration, developing agents were prepared from the N-nitroso compounds of Examples 1 to 4 as follows:

COMPOUND A

Preparation of

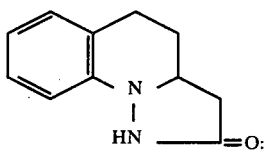

Ethyl 1-nitroso-1,2,3,4-tetrahydro-2-quinolylacetate obtained in Ex. 1 (14 gms.) was dissolved in dilute acetic acid (60 mls. water:80 mls. glacial acetic acid). The resulting solution was stirred at 16° C. in an ice bath under nitrogen, and 5 gms. of zinc dust were added in three portions. After the first addition, the temperature rose to 20° C. and the mixture was stirred in the ice bath for about 20 minutes until the temperature was about 16° C. The second portion was added, and the temperature rose to about 18° C. after which stirring in the ice bath was continued for another 15 minutes. After the third addition, the temperature rose from 13° to 17° C. The mixture was then removed from the ice bath and stirred at room temperature for about 30 minutes at which time the temperature was about 25° C.

The zinc was removed from the mixture by filtering through a sintered funnel. The filtrate was stripped at 55° C. leaving a gummy crystalline residue that was refrigerated overnight. The residue was taken up in chloroform/water, and the solvent was washed well, dried and stripped at 38° C. leaving a yellow oil (13.5 gms.). The oil was taken up in a mixture of hexane and benzene and the title compound was recovered as white crystals from the solvent mixture by filtering and drying in vacuuo over $P_2O_5$ at room temperature melting range 196°-197° C.

COMPOUND B

Preparation of

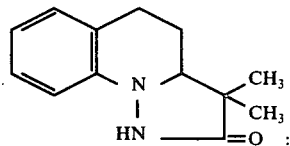

The nitroso compound prepared in Ex. 2 (1 gm) was dissolved in dilute acetic acid (8 mls. water: 11 mls. glacial acetic acid) in a water bath at a temperature of about 22° C. Zinc dust (1 gm) was added in portions to maintain the temperature at about 31°-32° C. After the addition was complete, the reaction mixture was heated at about 55° C. for 1 hour and then at 75° C. for about one-half hour. The reaction mixture was cooled, filtered to remove the zinc and stripped leaving a gummy solid. The solid was taken up in chloroform/water, and the solvent layer washed to neutral, dried and stripped to a brown oil. Crystallization of the oil from hexane/benzene gave a brown flocculant solid which was removed by filtration. Upon cooling and scratching, off-white crystals formed in the filtrate which were collected by filtration and chromatographed on silica gel using benzene, benzene/5% ether, benzene/10% ether and benzene/25% ether. The oil eluted with benzene/10% ether crystallized and the solid obtained was recrystallized to give the title compound as off-white crystals (melting range 148°-150° C.).

COMPOUND C

Preparation of

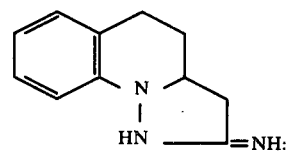

1-nitroso-1,2,3,4-tetrahydro-2-quinolylacetonitrile obtained in Ex. 3 (3 gms.) was dissolved in 20 mls. of glacial acetic acid and this solution added dropwise to a mixture of zinc dust in 20 mls. of water cooled to 15° C. and stirred under nitrogen. Addition was conducted at a rate to keep the temperature at about 15°-16° C. and the nitrile solution washed in with 5 mls. of glacial acetic acid. The reaction mixture was stirred in an ice bath for about one-half hour and then allowed to come to room temperature.

The zinc was removed by filtering through a sintered funnel under nitrogen. The filtrate was stripped under vacuum at about 40° C. to leave a solid that was taken up in chloroform/water under nitrogen. The water layer was pink—then blue—then colorless. The solvent layer was dried and stripped leaving a gummy white crystalline solid. A mixture of chloroform/benzene/hexane was added to the white crystalline solid and a gray solid crystallized which was dried in vacuo at room temperature. The gray solid was dissolved in benzene and the benzene solution filtered through a sintered funnel to remove remaining zinc. Shiny white plates slowly crystallized in the filtrate upon standing. The while plates were dried under vacuum at room temperature to give 1.0 ± gms. of the title compound (melting range 152°-154° C.).

COMPOUND D

Preparation of

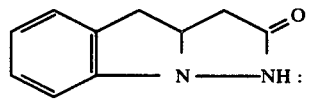

1. Ethyl 2-(N-nitrosoindolinyl) acetate (0.015–0.025 mole) was dissolved in 400 ml of a 50/50 mixture of 0.10M phosphate buffer and absolute ethanol. The dark solution was transferred to the cathode compartment of a water-jacketed electrolysis cell. Phosphate-ethanol mixture (60 ml) and 4N hydrochloric acid (5 ml) were added to the anode compartment. The solution was degassed for 15 minutes with nitrogen followed by the adjustment of pH of the cathode compartment to approximately 4.0 with 4N HCl. The reduction occurred at a mercury cathode (constant potential, 1.200 volts vs. saturated calomel electrode). A rotating platinum electrode was used as the anode. Initially the current ranged from 200–300 ma and after about 15-20 hours had decreased to 15 -20 ma. The reduction of substrate was monitored by polarographic analysis and a digital coulometer, the latter revealing a four electron process. In concluding the electrolysis the light yellow solution was transferred from the electrolysis cell, and the ethanol was evaporated. The aqueous mixture was extracted with chloroform, dried over anhydrous MgSO₄ and evaporated to give the hydrazine as a dark oil in 90-95% yield. The free base was converted to the hydrochloride salt with absolute ethanol saturated with HCl gas at 0° C. The salt was filtered and recrystallized from ethanol-ether to give a pale yellow solid, (m.p. 153°–155°). Reaction of the hydrazine salt with acetone give the corresponding Schiff base, m.p. 157°–158°.

2. The reduced compound (0.656 mmole) in CDCl₃ was placed in a pear-shaped flask and the CDCl₃ removed in vacuo. Quinoline (redistilled; 12.692 mmole) and a micro-stirrer bar were added and air removed by blowing a stream of nitrogen over the mixture for some time. Meanwhile an oil bath was preheated to 190°–195° C. Then the mixture was placed in the bath, stirred under nitrogen at 187°–195° C. (mostly around 193° C.) for 10 minutes, then removed and allowed to cool under nitrogen. As much quinoline as possible was distilled off in vacuo (bath temperature approximately 90° C., 0.27 mm) and the residue kept overnight under nitrogen. The mixture was shaken with saturated aqueous potassium bicarbonate to neutralize any hydrochlorides and then extracted with chloroform (4 ml and 2 × 1 ml). The dried chloroform extracts were washed once with saturated aqueous potassium bicarbonate (about 4 ml), dried with magnesium sulfate and evaporated first in a stream of nitrogen to remove chloroform and then in vacuo (bath temperature about 90° C., 0.27 mm) to remove as much quinoline as possible. The resulting dark brown gum comprising the title compound was taken up in CDCl₃ (0.9 ml) freed from traces of magnesium sulfate and after running a ¹³C nmr spectrum which confirmed the presence of the title compound, the compound was recovered by evaporation in a stream of nitrogen, mixing the partly crystallized residue with ether and then removing the ether (filterstick). The treatment with ether was repeated three times to remove as much quinoline as possible. To the residue was added chloroform (about 1 ml) and the mixture cooled to −60° C. and the chloroform removed. To the residual crystals was added chloroform, the mixture cooled again and the operation repeated. The crystalline residue (somewhat discolored prisms) was dried in vacuo leaving the title compound having a melting range of 150°–153.5° C.

To illustrate its usefulness as a reducing agent for silver halide, a few crystals of the title compound were placed on Velox paper (a photographic printing paper containing a silver chloride emulsion), and a few drops of 1N aqueous sodium hydroxide was placed on the crystals to dissolve them. The silver salt in the area of the dissolved crystals was reduced as evidenced by the appearance of a dark spot. No darkening occurred with the 1N sodium hydroxide alone.

To illustrate the usefulness of the ring-closed compounds in photography, Compound A was employed as a silver halide developing agent as follows:

A Polaroid Land Type 105 negative comprising a photosensitive silver halide emulsion was exposed in an automatic recording densitometer and processed by spreading a layer of processing composition approximately 0.0016 inch thick between the exposed emulsion and a superposed Polaroid Land Type 107 image-receiving element. The processing composition employed was prepared by adding 0.35 gm. of Compound A to 10 cc. of the following formulation:

| Water | 40 cc. |
|---|---|
| Potassium Hydroxide (Aqueous 45% w/w solution | 6.6 gm. |
| Potassium thiosulfate | 1.0 gm. |
| Sodium carboxymethyl cellulose | 2.0 gm. |

After an imbibition time of approximately 1 minute, the negative was stripped from the image-receiving element. The maximum and minimum reflection densities measured for the positive image were 1.0 and 0.12, respectively.

In a comparative example, the above procedure was repeated except that a molecular equivalent (0.3 gm./10 cc.) of 1-phenyl-3-pyrazolidone ("Phenidone"), a conventional developing agent was used instead of Compound A. The positive image obtained showed substantially less density as evidenced by maximum and minimum reflection densities of 0.4 and 0.03, respectively.

Since certain changes may be made in the above compositions and processes without departing from the scope of the invention herein involved, it is intended that all matter contained in the above description should be interpreted as illustrative and not in a limiting sense.

What is claimed is:

1. A compound of the formula

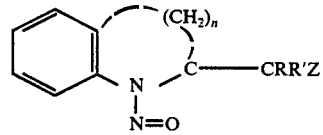

wherein R and R' each are hydrogen or lower alkyl having 1 to 4 carbon atoms, n is a positive integer 1 or 2 and Z is —CN or —COOR" wherein R" is lower alkyl having 1 to 4 carbon atoms.

2. A compound as defined in claim 1 wherein n is 1.

3. A compound of the formula

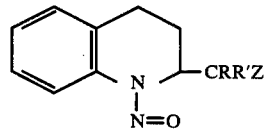

wherein R and R' each are hydrogen or lower alkyl having 1 to 4 carbon atoms and Z is —CN or —COOR" wherein R" is lower alkyl having 1 to 4 carbon atoms.

4. A compound as defined in claim 3 wherein R and R' are hydrogen.

5. A compound as defined in claim 3 wherein R and R' each are alkyl.

6. A composition as defined in claim 3 wherein Z is —CN.

7. A compound as defined in claim 3 wherein Z is —COOR".

8. The compound

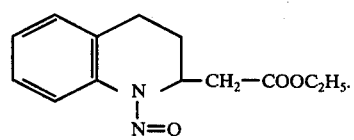

9. The compound
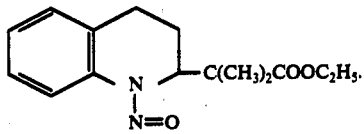
10. The compound
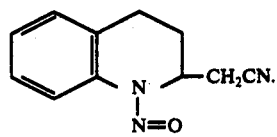
11. The compound
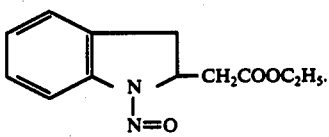
* * * * *